(12) United States Patent
Aoki et al.

(10) Patent No.: US 10,624,545 B2
(45) Date of Patent: Apr. 21, 2020

(54) BIOLOGICAL INFORMATION MONITOR

(71) Applicant: Nihon Kohden Corporation, Tokyo (JP)

(72) Inventors: Toshiki Aoki, Tokyo (JP); Shinji Yamamori, Tokyo (JP); Masayuki Inoue, Tokyo (JP); Katsuyuki Miyasaka, Tokyo (JP); Kiyoyuki Miyasaka, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 242 days.

(21) Appl. No.: 14/297,815

(22) Filed: Jun. 6, 2014

(65) Prior Publication Data
US 2014/0371546 A1 Dec. 18, 2014

(30) Foreign Application Priority Data
Jun. 13, 2013 (JP) ................................. 2013-124685

(51) Int. Cl.
| | | |
|---|---|---|
| *A61B 5/00* | (2006.01) | |
| *A61B 5/0205* | (2006.01) | |
| *A61B 5/08* | (2006.01) | |
| *A61B 5/021* | (2006.01) | |
| *A61B 5/083* | (2006.01) | |

(Continued)

(52) U.S. Cl.
CPC ............ *A61B 5/0205* (2013.01); *A61B 5/021* (2013.01); *A61B 5/082* (2013.01); *A61B 5/0836* (2013.01); *A61B 5/14551* (2013.01); *A61B 5/14552* (2013.01); *A61B 5/7203* (2013.01);

(Continued)

(58) Field of Classification Search
CPC combination set(s) only.
See application file for complete search history.

(56) References Cited

U.S. PATENT DOCUMENTS

| | | | | |
|---|---|---|---|---|
| 4,450,436 A | * | 5/1984 | Massa | ...................... G08B 1/08 181/139 |
| 5,738,106 A | | 4/1998 | Yamamori et al. | |

(Continued)

FOREIGN PATENT DOCUMENTS

| | | |
|---|---|---|
| JP | 5-317269 A | 12/1993 |
| JP | 2001-245856 A | 9/2001 |

(Continued)

OTHER PUBLICATIONS

Communication, dated Aug. 13, 2014, issued by the European Patent Office in counterpart Patent Application No. 14171447.7-1657.

(Continued)

*Primary Examiner* — Christopher A Flory
*Assistant Examiner* — Shirley X Jian
(74) *Attorney, Agent, or Firm* — Sughrue Mion, PLLC

(57) ABSTRACT

A biological information monitor includes: a measuring section which is configured to measure biological information having a periodically changing value; a sound outputting section which is configured to output a sound including a first sound and a second sound, in synchronization with a period of the biological information; and a sound controlling section which is configured to cause the second sound to be output in succession to the first sound, and which is configured to change the second sound in accordance with a value of the biological information.

7 Claims, 4 Drawing Sheets

(51) Int. Cl.
*A61B 5/1455* (2006.01)
*A61B 7/04* (2006.01)

(52) U.S. Cl.
CPC .............. *A61B 5/746* (2013.01); *A61B 7/04* (2013.01); *A61B 5/7405* (2013.01)

(56) References Cited

U.S. PATENT DOCUMENTS

| | | | |
|---|---|---|---|
| 8,475,385 B2 * | 7/2013 | Watson | ................ A61B 5/7415 600/485 |
| 2004/0243016 A1 | 12/2004 | Sanderson et al. | |
| 2006/0111621 A1 | 5/2006 | Coppi et al. | |
| 2008/0114216 A1 | 5/2008 | Watson | |
| 2012/0116235 A1 * | 5/2012 | Trumble | .............. A61B 5/7415 600/485 |

FOREIGN PATENT DOCUMENTS

| | | |
|---|---|---|
| JP | 3273295 B2 | 4/2002 |
| JP | 2004-194996 A | 7/2004 |
| JP | 2004-538115 A | 12/2004 |
| JP | 2008-516701 A | 5/2008 |
| WO | 2014007927 A1 | 1/2014 |

OTHER PUBLICATIONS

Office Action dated Dec. 20, 2016 issued by the Japanese Patent Office in counterpart Japanese Patent Application No. 2013-124685.
Office Action dated Aug. 1, 2017 by the Japanese Patent Office in counterpart Japanese Patent Application No. 2013-124685.
Communication dated Sep. 4, 2018, issued by the Japanese Patent Office in counterpart Japanese Patent Application No. 2017-208447.
Communication dated Jan. 5, 2018, from the Japanese Patent Office in counterpart application No. 2013-124685.
Communication dated Jun. 5, 2018, issued by the European Patent Office in counterpart European Application No. 18159494.6.
Communication dated Oct. 2, 2018 issued by the Japanese Patent Office in counterpart Japanese Application No. 2013-124685.

* cited by examiner

FIG. 2

| MEASURING VALUE | CHANGE OF SOUND |
|---|---|
| HIGHER | S1 ○ → ○ S2 |
| NORMAL RANGE | S1 ○ → ○ S2 |
| LOWER | S1 ○ ↘ ○ S2 |

FIG. 4

| MEASURING VALUE | CHANGE OF SOUND |
|---|---|
| HIGHER (HIGHER DEGREE OF EMERGENCY) | S1 → S2 → S3 (ascending) |
| HIGHER (LOWER DEGREE OF EMERGENCY) | S1 → S2 (ascending) |
| NORMAL RANGE | S1 → S2 (level) |
| LOWER (LOWER DEGREE OF EMERGENCY) | S1 → S2 (descending) |
| LOWER (HIGHER DEGREE OF EMERGENCY) | S1 → S2 → S3 (descending) |

BIOLOGICAL INFORMATION MONITOR

CROSS-REFERENCE TO RELATED APPLICATION(S)

This application is based upon and claims the benefit of priority from prior Japanese patent application No. 2013-124685, filed on Jun. 13, 2013, the entire contents of which are incorporated herein by reference.

BACKGROUND

The presently disclosed subject matter relates to an apparatus for monitoring biological information of a patient or the like.

Among apparatuses for measuring biological information having a periodically changing value such as the arterial oxygen saturation (SpO2) or the end-tidal carbon dioxide concentration (ETCO2), known is an apparatus which outputs a sound in synchronization with the period of the biological information (for example, see Japanese Patent No. 3273295).

In the apparatus disclosed in Japanese Patent No. 3273295, in order to enable the user to identify the measurement value without requiring visual reading of the value, the tone scale of the output sound is changed in accordance with the value of biological information of the measurement target. However, it is difficult for a user having no sense of absolute pitch to discriminate small differences between scales to identify the measurement value.

SUMMARY

The presently disclosed subject matter may provide a technique which, in a biological information monitor which outputs a sound corresponding to a measurement value, enables the user to identify the measurement value without depending on the sense of absolute pitch of the user.

The biological information monitor may comprise: a measuring section which is configured to measure biological information having a periodically changing value; a sound outputting section which is configured to output a sound including a first sound and a second sound, in synchronization with a period of the biological information; and a sound controlling section which is configured to cause the second sound to be output in succession to the first sound, and which is configured to change the second sound in accordance with a value of the biological information.

The sound controlling section may change at least one of a scale, tone, sound number, length, and volume of the second sound.

In a case where the value of the biological information is outside a normal range, the sound controlling section may change the second sound.

The sound controlling section may control the sound so that the first sound is continuously changed to the second sound.

The biological information may be one of an end-tidal carbon dioxide concentration, a blood oxygen saturation, and an invasive blood pressure.

BRIEF DESCRIPTION OF THE DRAWINGS

FIG. 2 is a view illustrating a sound control process which is performed by the monitor apparatus.

FIG. 4 is a view illustrating another modification of the sound control process which is performed by the monitor apparatus.

DETAILED DESCRIPTION OF EXEMPLARY EMBODIMENTS

Figure 1:
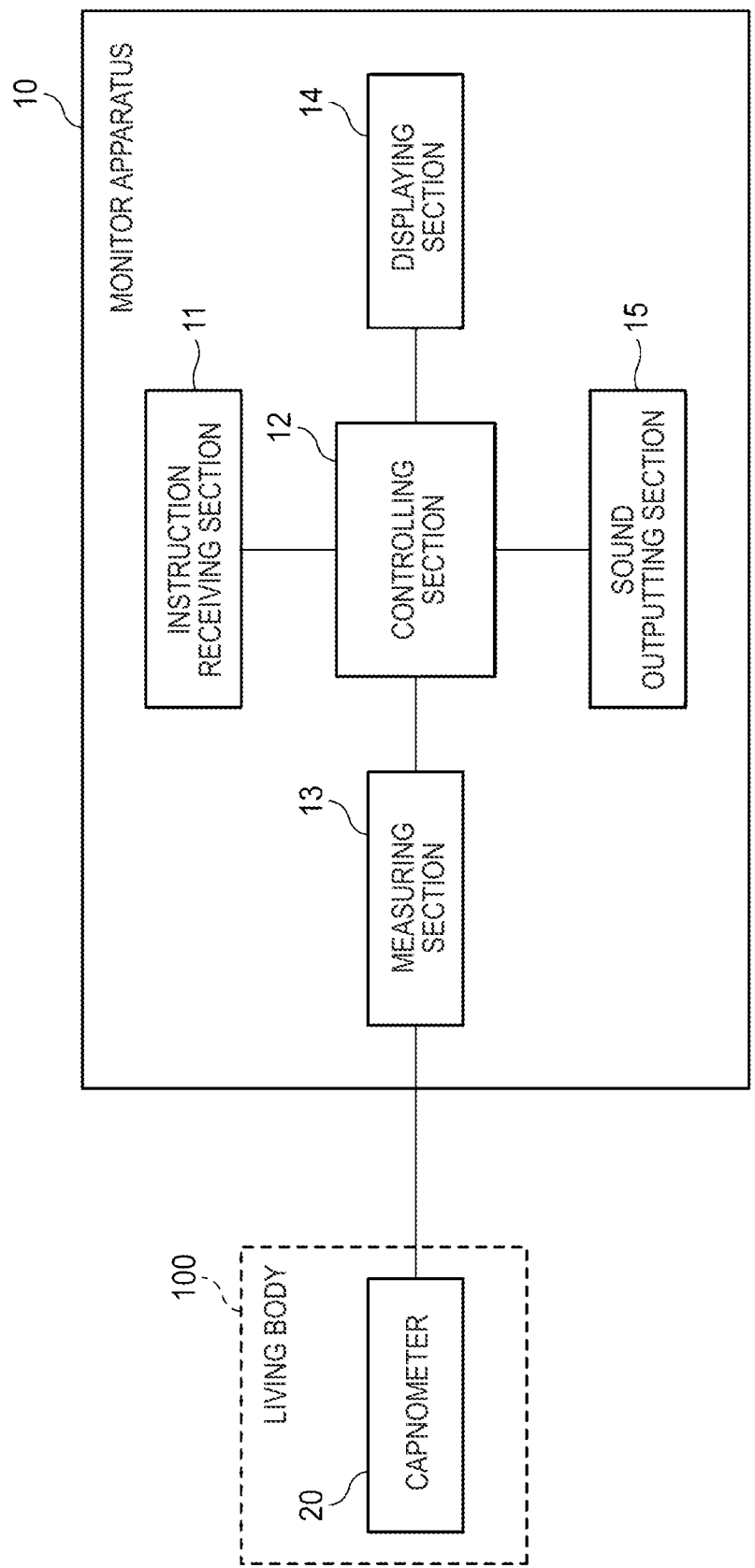
FIG. 1 is a functional block diagram showing the configuration of a monitor apparatus of an embodiment of the presently disclosed subject matter.

Hereinafter, an embodiment of the presently disclosed subject matter will be described in detail with reference to the accompanying drawings. In the drawings which will be used in the following description, the scale is adequately changed in order to draw components in a recognizable size.

FIG. 1 is a functional block diagram showing the configuration of a monitor apparatus 10 (an example of the biological information monitor) of an embodiment of the presently disclosed subject matter. The monitor apparatus 10 includes an instruction receiving section 11, a controlling section 12, a measuring section 13, a displaying section 14, and a sound outputting section 15.

The instruction receiving section 11 is a man-machine interface which is disposed on the outer surface of the monitor apparatus 10, and configured so as to be able to receive instructions which are input by the user in order to cause the monitor apparatus 10 to perform a desired operation.

The controlling section 12 includes a CPU which executes various calculation processes, a ROM which stores various control programs, a RAM which is used as a work area for storing data and executing the programs, and the like, and executes various controls in the monitor apparatus 10. The controlling section 12 is communicably connected to the instruction receiving section 11. The instruction receiving section 11 supplies a signal corresponding to received instructions, to the controlling section 12.

The measuring section 13 is communicably connected to a capnometer 20 which is disposed outside the monitor apparatus 10. The capnometer 20 is a sensor which is attached to a living body 100 to measure the end-tidal carbon dioxide concentration (ETCO2). The ETCO2 is an example of biological information which periodically changes in accordance with the respiration of the living body 100. The capnometer 20 outputs a signal corresponding to the value of the ETCO2.

The measuring section 13 receives the signal which is output from the capnometer 20 to acquire the measurement value of the ETCO2. The measuring section 13 is communicably connected to the controlling section 12, and supplies the acquired measurement value to the controlling section 12.

The displaying section 14 is a man-machine interface which is disposed on the outer surface of the monitor apparatus 10, and includes a display device which displays visible information. The displaying section 14 is communicably connected to the controlling section 12. The controlling section 12 produces a signal corresponding to the information to be displayed, based on the measurement value of the ETCO2 which is acquired from the measuring section 13, and supplies the signal to the displaying section 14. The displaying section 14 displays information corresponding to the supplied signal. The information is displayed in an adequate mode such as a numerical value, characters, a waveform, or a color.

The sound outputting section 15 is configured by including a speaker, and communicably connected to the controlling section 12. The controlling section 12 produces a signal corresponding to the sound to be output, based on the measurement value of the ETCO2 which is acquired from the measuring section 13, and supplies the signal to the sound outputting section 15. The sound outputting section 15 outputs a sound corresponding to the supplied signal.

Specifically, a sound including a first sound and a second sound is output in synchronization with the period of the biological information by the sound outputting section 15. The measurement value of biological information periodically varies, and also its period varies. For example, the measurement value of the ETCO2 periodically increases or decreases in accordance with the respiration of the subject. However, the period of the respiration is not constant, and therefore also the increasing/decreasing period of the measurement value is not constant. In the specification, "synchronization" means that a predetermined reference is determined within the variation range of the measurement value, and a timing when the measurement value coincides with the reference is set as a trigger of the sound output.

Namely, the controlling section 12 produces a signal causing the sound outputting section 15 to output the sound including the first and second sounds, at a timing when the measurement value of the ETCO2 acquired from the measuring section 13 coincides with the predetermined reference. The signal is supplied from the controlling section 12 to the sound outputting section 15, and then output as a synchronous sound from the sound outputting section 15.

The controlling section 12 functions as an example of the sound controlling section, and causes the second sound to be output in succession to the first sound. That is, the synchronous sound is output from the sound outputting section 15 while setting the first sound and the second sound subsequent thereto as one unit.

The controlling section 12 is configured so as to change the second sound in accordance with the measurement value of the ETCO2. FIG. 2 shows a table illustrating the process which is performed by the controlling section 12. In the table, the circular symbols denoted by a reference numeral S1 indicate the first sound, and those denoted by a reference numeral S2 indicate the second sound. The higher a circular symbol is located, the higher the scale is, and the lower a circular symbol is located, the lower the scale is.

In the embodiment, measurement values of the ETCO2 are classified into three ranges. In the case where the measurement value is from 35 to 40 mmHg, it is considered that the measurement value is in the normal range. In the case where the measurement value is higher than 40 mmHg, it is considered that the measurement value is an abnormal value which is higher than the normal range. In the case where the measurement value is lower than 35 mmHg, it is considered that the measurement value is an abnormal value which is lower than the normal range.

When the measurement value is within the normal range, the controlling section 12 produces a sound signal so that, in succession to the first sound S1, the second sound S2 which is on the same scale as the first sound is output (for example, mi->mi). When the measurement value is an abnormal value which is higher than the normal range, the controlling section 12 produces a sound signal so that, in succession to the first sound S1, the second sound S2 which is higher in scale than the first sound is output (for example, mi->so). At this time, a mode where the second sound S2 of the higher scale is output a plurality of times (for example, mi->so->so), or that where the second sound S2 is output for a time period that is longer than that in a usual case (for example, mi->s--o--) may be employed. When the measurement value is an abnormal value which is lower than the normal range, the controlling section 12 produces a sound signal so that, in succession to the first sound S1, the second sound S2 which is lower in scale than the first sound is output (for example, mi->do). At this time, a mode where the second sound S2 of the lower scale is output a plurality of times (for example, mi->do->do), or that where the second sound S2 is output for a time period that is longer than that in a usual case (for example, mi->d--o--) may be employed.

In order to distinguish the scale of a synchronous sound which is output as a single tone, the sense of absolute pitch is required. Even when relationships between the scale of a synchronous sound and a measurement value are previously known, therefore, the measurement value is hardly identified from the scale of the heard synchronous sound. According to the configuration of the embodiment, however, the synchronous sound to includes the first sound S1 and the second sound S2, and the second sound S2 is changed in accordance with the measurement value. When the difference between the first sound S1 and the second sound S2 is to be distinguished, the sense of absolute pitch is not required. Therefore, the measurement value is easily identified based on the synchronous sound.

In the embodiment, particularly, the controlling section 12 changes the scale of the second sound S2 in accordance with the measurement value. When the scale change is to be identified, the sense of absolute pitch is not required. Therefore, the measurement value is identified more easily based on the synchronous sound. Moreover, the level of the measurement value and the pitch of the scale can be easily corresponded with each other. Consequently, the level of the measurement value is identified more intuitively.

In the embodiment, in the case where the measurement value is outside the normal range, the controlling section 12 changes the second sound S2. Therefore, the user can identify a change in the subject's condition based only on the fact that the second sound S2 is changed from the first sound S1. This enables the user to promptly cope with the change in the subject's condition.

The embodiment has been described in order to facilitate understanding of the presently disclosed subject matter, and is not intended to limit the presently disclosed subject matter. to It is a matter of course that the presently disclosed subject matter may be changed or improved without departing the spirit thereof, and includes equivalents thereof.

The sensor which is to be attached to the living body 100 is not limited to the capnometer 20. In place of or in addition to the capnometer 20, any adequate sensor may be used as far as it is a sensor which senses biological information having a periodically changing value. For example, a pulse oximeter for measuring the arterial oxygen saturation (SpO2) the value of which periodically changes in accordance with the pulse may be used. Alternatively, a catheter for measuring the invasive blood pressure the value of which similarly periodically changes in accordance with the pulse may be used.

In the embodiment, the scale of the second sound S2 is changed in accordance with the measurement value. Alternatively, another attribute relating to a sound may be changed in combination with the change of the scale.

Figure 3A:
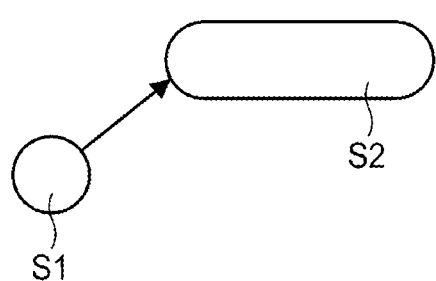
FIGS. 3A to 3D are views illustrating modifications of the sound control process which is performed by the monitor apparatus.

FIG. 3A shows an example in which the length of the second sound S2 is changed. In the case where the measurement value acquired by the measuring section 13 is outside the normal range, the controlling section 12 produces the sound signal so that the scale is changed, and the length of the second sound S2 is longer than that of the first sound S1.

According to the configuration, it is possible to recognize a change in the subject's condition, based only on to the fact that the length of the second sound S2 is longer than that of the first sound S1. Moreover, the output of the second sound S2 after the scale is changed is continued for a long time period, and therefore the change of the scale is easily recognized.

Figure 3B:
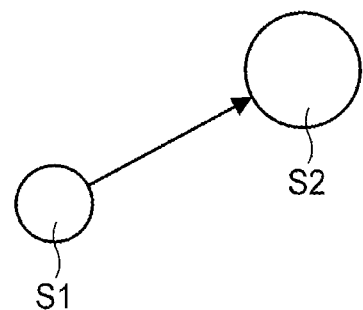

FIG. 3B shows an example in which the volume of the second sound S2 is changed. In the case where the measurement value acquired by the measuring section 13 is outside the normal range, the controlling section 12 produces the sound signal so that the scale is changed, and the volume of the second sound S2 is larger than that of the first sound S1.

According to the configuration, it is possible to recognize a change in the subject's condition, based only on the fact that the volume of the second sound S2 is larger than that of the first sound S1. Moreover, the output of the second sound S2 after the scale is changed is performed at larger volume, and therefore the change of the scale is easily recognized.

Alternatively, a configuration may be employed where only the volume of the second sound S2 is changed while the scale of the second sound S2 is maintained to be identical with that of the first sound S1. In the case where the measurement value is an abnormal value which is higher than the normal range, for example, the volume of the second sound S2 may be made larger than that of the first sound S1, and, in the case where the measurement value is an abnormal value which is lower than the normal range, the volume of the second sound S2 may be made smaller than that of the first sound S1.

Figure 3C:
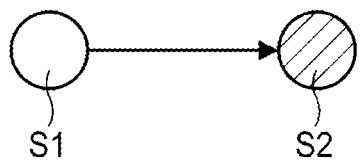

FIG. 3C shows an example in which the tone of the second sound S2 is changed. In the case where the measurement value acquired by the measuring section 13 is outside the normal range, the controlling section 12 produces the sound signal so that the tone of the second sound S2 is different from that of the first sound S1 while the scale is maintained.

The terms "the tone of the sound is different" mean that, even when the scales of sounds are identical with each other, the sounds are heard indifferent tones. For example, different tones are obtained by outputting the first sound S1 in the sound of a wind instrument, and outputting the second sound S2 in the sound of a string instrument.

According to the configuration, it is possible to recognize a change in the subject's condition, based only on the fact that the tone of the second sound S2 is different from that of the first sound S1. When the tone change is to be recognized, the sense of absolute pitch is not required. Therefore, the tone change is easily recognized.

In the embodiment, each of the first sound S1 and the second sound S2 is configured by a single tone. As in a chord tone, however, at least one of the first sound S1 and the second sound S2 may be formed by superimposing a plurality of sounds of different scales on each other. In the specification, also to a change from a single tone to a chord tone, that from a chord tone to a single tone, and that from a chord tone to another chord tone are included in the case of "the scale is changed".

Figure 3D:
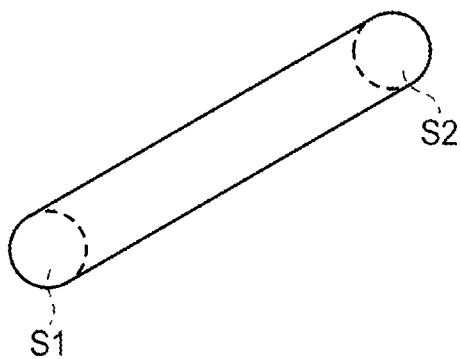

In the embodiment, the first sound S1 and the second sound S2 are discontinuously output. As shown in FIG. 3D, alternatively, the synchronous sound may be output so that the first sound S1 is continuously changed to the second sound S2. In the alternative, the change of the synchronous sound can be recognized more easily.

In the embodiment, measurement values are classified into the three ranges, and the synchronous sound is configured by the two sounds S1, S2. However, both the classification number of measurement values, and the number of sounds constituting the synchronous sound are arbitrarily selected as far as the numbers are plural.

As shown in FIG. 4, for example, measurement values may be classified into five ranges. In this case, each of the range of an abnormal value which is higher than the normal range, and that of an abnormal value which is lower than the normal range is divided into subranges of higher and lower degrees of emergency. In the case where the measurement value is in one of the abnormal ranges of the higher degree of emergency, the controlling section 12 produces the sound signal so that a third sound S3 is output in succession to the second sound S2. The relationships between the level of the measurement value and to the pitch of the scale are identical with those of the embodiment.

According to the configuration, the user can easily recognize the increase of the degree of emergency of the subject's condition, based on the fact that the number of sounds constituting the synchronous sound is increased. When the number of sounds is added to the items which cause a sound to be changed, the range of measurement values to be correlated can be further finely divided.

According to an aspect of the presently disclosed subject matter, the biological information monitor includes a measuring section which is configured to measure biological information having a periodically changing value, a sound outputting section which is configured to output a sound including a first sound and a second sound, in synchronization with a period of the biological information, and a sound controlling section which is configured to cause the second sound to be output in succession to the first sound, and which is configured to change the second sound in accordance with a value of the biological information. According to this configuration, the sound (synchronous sound) which is output in synchronization with the period of the biological information includes the first sound and the second sound, and the second sound is changed in accordance with the measurement value. In identifying the difference between the first and second sounds, the sense of to absolute pitch is not necessary. Therefore, the measurement value can be easily identified based on the synchronous sound.

The sound controlling section may change at least one of a scale, tone, sound number, length, and volume of the second sound. In a case where the scale is changed, when the change is to be identified, particularly, the sense of absolute pitch is not necessary. Therefore, the measurement value can be identified more easily based on the synchronous sound. The level of the measurement value and the pitch of the scale can be easily made corresponding to each other. Consequently, the level of the measurement value can be identified more intuitively.

In a case where the value of the biological information is outside a normal range, the sound controlling section may change the second sound. Therefore, the user can recognize a change in the subject's condition based only on the fact that the second sound is changed from the first sound. This enables the user to promptly cope with the change in the subject's condition.

The sound controlling section may control the sound so that the first sound is continuously changed to the second sound. In this case, the change of the synchronous sound can be recognized more easily.

The biological information may be one of an end-tidal carbon dioxide concentration, a blood oxygen saturation, and an invasive blood pressure.

What is claimed is:

1. A biological information monitor comprising:
   at least one hardware processor configured to implement controlling:
      a measuring section which is configured to measure biological information having a periodically changing value;
      a sound controlling section which is configured to set a first part and a second part of a sound as a single unit;
      a sound outputting section, comprising a speaker, which is configured to output the sound, the sound including the first part and the second part, set as the single unit such that output of the sound is periodically repeated in synchronization with a period of the biological information; and
      wherein the sound controlling section is configured to cause the second part to be output in succession to the first part,
   wherein, when the value of the biological information is within a normal range, the sound outputting section outputs the sound, and the sound controlling section causes the second part of the sound to be identical to the first part of the sound in at least one of a scale, tone, length, and volume, and
   wherein, when the value of the biological information is outside the normal range, the sound outputting section outputs the sound, and the sound controlling section causes the second part of the sound to be different from the first part of the sound in at least one of a scale, tone, length, and volume.

2. The biological information monitor according to claim 1, wherein the sound controlling section controls the sound so that the first part and the second part are continuously output.

3. The biological information monitor according to claim 1, wherein the biological information is one of an end-tidal carbon dioxide concentration, a blood oxygen saturation, and an invasive blood pressure.

4. The biological information monitor according to claim 1, wherein the sound controlling section controls the sound so that the first part and the second part are discontinuously output.

5. A biological information monitoring apparatus, comprising:
   a speaker; and
   a processor configured to:
      set a first part and a second part of a sound as a single unit;
      control the speaker to output the sound, the sound including the first part and the second part, set as the single unit such that output of the sound is periodically repeated in synchronization with a period of biological information, the biological information which is measured by a sensor and which has a periodically changing value,
   wherein, when the value of the biological information is within a normal range, the processor controls the speaker to output the sound, and causes the second part of the sound to be identical to the first part of the sound in at least one of a scale, tone, length, and volume, and
   wherein, when the value of the biological information is outside the normal range, the processor controls the speaker to output the sound, and causes the second part of the sound to be different from the first part of the sound in at least one of a scale, tone, length, and volume.

6. The biological information monitoring apparatus according to claim 5, wherein the processor is configured to control the sound so that the first part and the second part are continuously output.

7. The biological information monitoring apparatus according to claim 5, wherein the biological information is one of an end-tidal carbon dioxide concentration, a blood oxygen saturation, and an invasive blood pressure.

* * * * *